United States Patent
Feng et al.

(10) Patent No.: US 6,927,264 B2
(45) Date of Patent: Aug. 9, 2005

(54) METAL COMPLEXES AND POLYMERIZATION PROCESS USING SAME

(75) Inventors: Shaoguang Feng, Midland, MI (US); Ravi B. Shankar, Midland, MI (US); Francis J. Timmers, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/855,815

(22) Filed: May 27, 2004

(65) Prior Publication Data

US 2004/0249092 A1 Dec. 9, 2004

Related U.S. Application Data

(60) Provisional application No. 60/473,655, filed on May 28, 2003.

(51) Int. Cl.[7] ............................... C08F 4/16; C08F 7/00
(52) U.S. Cl. ...................... 526/172; 526/161; 526/126; 526/346; 526/348; 556/52; 556/5; 556/11
(58) Field of Search ................................. 526/126, 172, 526/161, 347.1, 346, 348, 160, 170, 943; 556/52, 51, 11, 53

(56) References Cited

U.S. PATENT DOCUMENTS

| | | | |
|---|---|---|---|
| 5,321,106 A | 6/1994 | LaPointe | 526/126 |
| 5,374,696 A | 12/1994 | Rosen et al. | 526/126 |
| 5,470,993 A | 11/1995 | Devore et al. | 556/11 |
| 5,486,632 A | 1/1996 | Devore et al. | 556/11 |
| 5,541,349 A | 7/1996 | Wilson et al. | 556/10 |
| 5,703,187 A | 12/1997 | Timmers | 526/202 |
| 5,721,185 A | 2/1998 | LaPointe et al. | 502/117 |
| 6,150,297 A | 11/2000 | Campbell, Jr. et al. | 502/152 |
| 6,232,260 B1 * | 5/2001 | Nagy et al. | 502/155 |
| 6,268,444 B1 | 7/2001 | Klosin et al. | 526/127 |
| 6,559,251 B1 * | 5/2003 | Mack et al. | 526/127 |
| 6,683,150 B1 * | 1/2004 | Meverden et al. | 526/351 |
| 6,838,410 B2 * | 1/2005 | Wang et al. | 502/103 |
| 2002/0151662 A1 | 10/2002 | Campbell, Jr. et al. | 526/127 |
| 2002/0165329 A1 * | 11/2002 | Klosin et al. | 526/126 |

FOREIGN PATENT DOCUMENTS

| | | |
|---|---|---|
| WO | WO97/15583 | 5/1997 |
| WO | WO98/06728 | 2/1998 |
| WO | WO98/27102 | 6/1998 |
| WO | WO01/144318 | 6/2001 |
| WO | WO01/47939 | 7/2001 |
| WO | WO01/48039 | 7/2001 |
| WO | WO01/48040 | 7/2001 |
| WO | WO01/53360 | 7/2001 |

OTHER PUBLICATIONS

Organometallics (2001) 20, 132, 2663–2665.

* cited by examiner

*Primary Examiner*—David W. Wu
*Assistant Examiner*—Rip A Lee

(57) ABSTRACT

A metal complex useful as a component of a catalyst composition for addition polymerizations comprising an anionic, polycyclic, fused ring ligand system containing at least 4 fused rings, at least one such ring comprising at least one heteroatom, said ligand being bonded to M by means of delocalized π-electrons and an addition polymerization process using the same.

8 Claims, No Drawings

METAL COMPLEXES AND POLYMERIZATION PROCESS USING SAME

CROSS-REFERENCE TO RELATED APPLICATION

This application claims benefit of priority from provisional application 60/473,655, filed May 28, 2003.

BACKGROUND OF THE INVENTION

This invention relates to certain metal complexes useful as catalyst components for polymerization of addition polymerizable monomers, especially olefins. In addition, the invention relates to an improved polymerization process employing such metal complexes as one component of an addition polymerization catalyst.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106; 5,721,185, 5,374,696, 5,470,993, 5,541,349, and 5,486,632, as well as WO97/15583, and WO98/27102 (97 PCT 19463). Such catalysts based on a cyclopentaphenanthreneyl ring system ligand are disclosed in U.S. Pat. No. 6,150,297. Metallocenes with heteroatom containing delocalized fused ring systems are disclosed in WO01/53360, WO01/44318, WO01/47939, WO01/48039, WO01/48040, WO98/06728 and U.S. Pat. No. 6,268,444, and suggested in U.S. Ser. No. 10/124,269, published as U.S. Pat. No. 2002/0151662, on Oct. 17, 2002.

SUMMARY OF THE INVENTION

According to the present invention there is provided a metal complex corresponding to the formula: $CpZMX_xL_1X'_{x'}$. (IA);

where Cp is an anionic, polycyclic, fused ring ligand system containing at least 4 fused rings, at least one such ring comprising at least one heteroatom, said Cp group being bonded to M by means of delocalized $\pi$-electrons;

M is titanium, zirconium or hafnium in the +2, +3 or +4 formal oxidation state;

Z is either a cyclic or noncyclic ligand group containing delocalized $\pi$-electrons, including a second polycyclic ring system group as herein previously disclosed for Cp, said Z being bonded to M by means of delocalized $\pi$-electrons and optionally covalently bonded to Cp through a divalent bridging group, or Z is a divalent moiety lacking in delocalized $\pi$-electrons that is covalently bonded to Cp and M, or such a moiety comprising one $\sigma$-bond by which it is bonded to Cp, and a neutral two electron pair able to form a coordinate-covalent bond to M;

X is a monovalent anionic ligand group having up to 60 atoms other than hydrogen;

L independently each occurrence is a neutral ligating compound having up to 20 atoms;

X' is a divalent anionic ligand group having up to 60 atoms;

x is 0, 1, 2, or 3;

t is a number from 0 to 2; and x' is 0 or 1.

In addition according to the invention there is provided a process for the polymerization of addition polymerizable monomers, especially $C_{2-20}$ olefin monomers or mixtures thereof, comprising contacting said monomer or mixture of monomers under addition polymerization conditions with a catalyst composition comprising the reaction product or admixture of:

(A) a metal complex corresponding to the formula: $CpZMX_xL_1X'_{x'}$. (IA);

where Cp is an anionic, polycyclic, fused ring ligand system containing at least 4 fused rings, at least one such ring comprising at least one heteroatom, preferably a Group 15 or 16 heteroatom, said Cp group being bonded to M by means of delocalized $\pi$-electrons;

M is titanium, zirconium or hafnium in the +2, +3 or +4 formal oxidation state;

Z is either a cyclic or noncyclic ligand group containing delocalized $\pi$-electrons, including a second polycyclic ring system group as herein previously disclosed for Cp, said Z being bonded to M by means of delocalized $\pi$-electrons and optionally covalently bonded to Cp through a divalent bridging group, or Z is a divalent moiety lacking in delocalized $\pi$-electrons that is covalently bonded to Cp and M, or such a moiety comprising one $\sigma$-bond by which it is bonded to Cp, and a neutral two electron pair able to form a coordinate-covalent bond to M;

X is a monovalent anionic ligand group having up to 60 atoms other than hydrogen;

L independently each occurrence is a neutral ligating compound having up to 20 atoms;

X' is a divalent anionic ligand group having up to 60 atoms;

x is 0, 1, 2, or 3;

t is a number from 0 to 2, and x' is 0 or 1; and (B) a cocatalyst able to form an active polymerization catalyst species in combination with (A).

Use of the present polymerization process is especially efficient in production of olefin homopolymers, copolymers of two or more olefins, in particular, copolymers of ethylene and a vinylaromatic monomer, such as styrene, and interpolymers of three or more polymerizable monomers over a wide range of polymerization conditions, and especially at elevated temperatures. The process is especially suited for the formation of copolymers of ethylene and vinylaromatic monomers such as styrene (ES interpolymers) and copolymers of ethylene, propylene and styrene UPS interpolymers).

The catalyst compositions may also include a support material and be used in olefin polymerization processes in a slurry or in the gas phase. The catalyst components may be prepolymerized with one or more olefin monomers in situ in a polymerization reactor or in a separate process with intermediate recovery of the prepolymerized catalyst prior to the primary polymerization process, as well.

DETAILED DESCRIPTION

All reference to the Periodic Table of the Elements herein shall refer to the Periodic Table of the Elements, published and copyrighted by CRC Press, Inc., 1999. Also, any reference to a Group or Groups shall be to the Group or Groups as reflected in this Periodic Table of the Elements using the IUPAC system for numbering groups. For purposes of United States patent practice, the contents of any patent, patent application or publication referenced herein is hereby incorporated by reference in its entirety herein, especially with respect to its disclosure of organometallic structures, synthetic techniques and general knowledge in the art.

If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise, refers to the listed members individually as well as in any combination.

As used herein the term "aromatic" refers to a polyatomic, cyclic, ring system containing (4δ+2) π-electrons, wherein δ is an integer greater than or equal to 1. The term "fused" as used herein with respect to a ring system containing two or more polyatomic, cyclic rings means that with respect to at least two rings thereof, at least one pair of adjacent atoms is included in both rings.

Preferred Cp groups herein include polycyclic, fused ring ligand groups containing at least 4 fused rings, at least one of which comprises at least one N, O, P or S atom located in the ring, more preferably N, and most preferably N in a single ring and not shared between two or more rings, and optionally substituted with one or more substituents selected from hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylenephosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl groups, said Cp having up to 40 atoms not counting hydrogen atoms, and optionally two or more of the foregoing substituents may together form a divalent derivative.

In the foregoing metal complexes Z, if not a Cp group, preferably comprises boron, or a member of Group 14 of the Periodic Table of the Elements, and also nitrogen, phosphorus, sulfur or oxygen, and has up to 30 atoms, not counting hydrogen.

Preferred metal complexes for use according to the present invention correspond to the formula:

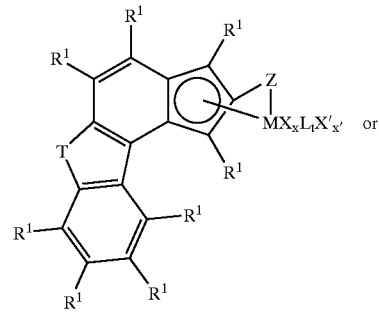

(IB)

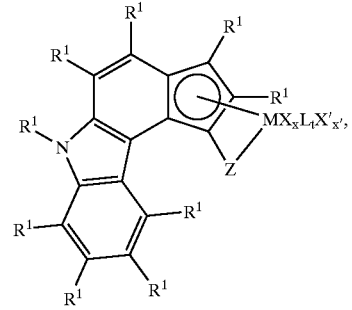

(IC)

where M is titanium, zirconium or hafnium in the +2, +3 or +4 formal oxidation state;

T is —$NR^4$— or —O—;

$R^1$ independently each occurrence is hydrogen, hydrocarbyl, trihydrocarbylsilyl, trihydrocarbylsilylhydrocarbyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring;

$R^4$ is hydrocarbyl, silyl, germyl, or halohydrocarbyl or up to 10 atoms not counting hydrogen;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

t is a number from 0 to 2, and x' is 0 or 1.

More preferred metal complexes for use in the present invention correspond to the following formulas:

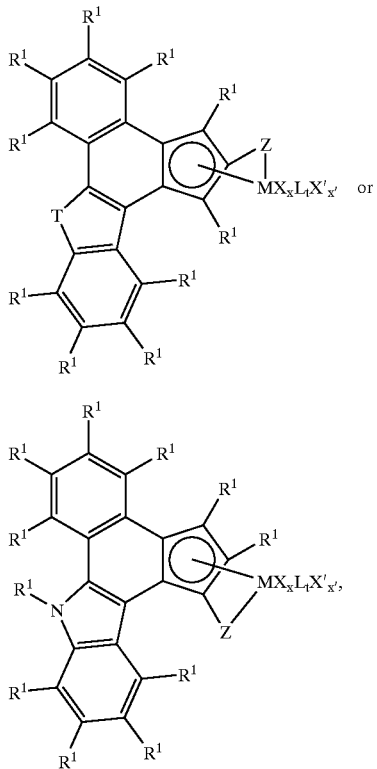

wherein,

M is titanium in the +2, +3 or +4 formal oxidation state;

T is as previously defined with respect to formulas IB and IC, preferably —NR$^4$—;

R$^1$ independently each occurrence is hydrogen or C$_{1-10}$ hydrocarbyl, and optionally two or more of the foregoing adjacent R$^1$ groups may together form a divalent derivative thereby forming a saturated or unsaturated fused ring;

R$^4$ is C$_{1-4}$ alkyl;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

t is a number from 0 to 2; and x' is 0 or 1.

Most preferred metal complexes for use in the present invention correspond to the formula:

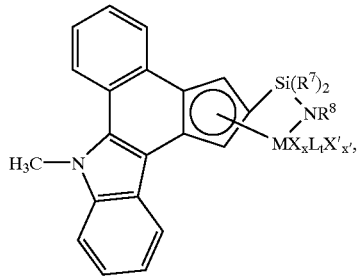

wherein,

M is titanium in the +2 or +4 formal oxidation state;

R$^7$ independently each occurrence is C$_{1-10}$ hydrocarbyl, preferably methyl or p-C$_{1-4}$ alkyl-substituted phenyl;

R$^8$ is C$_{1-10}$ alkyl or cycloalkyl, preferably t-butyl;

X is a chloride, tri(C$_{1-4}$alkyl)silyl, C$_{1-4}$ alkyl, or benzyl;

L independently each occurrence is a neutral ligating compound having up to 20 atoms;

X' is 1,4-bis(dimethylsilyl)phenylene; 1,4-butanediyl or (2,3-dimethyl-1,4-butanediyl);

x' is 0 or 2;

t is a number from 0 to 2; and x' is 0 or 1.

In the foregoing metal complexes IB–IF, preferred L groups are carbon monoxide; phosphines, especially trimethylphosphine, triethylphosphine, triphenylphosphine and bis(1,2-dimethylphosphino)ethane; P(OR$^4$)$_3$, wherein R$^4$ is C$_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including such neutral diene L groups are those wherein the metal is in the +2 formal oxidation state.

Further in reference to the metal complexes, X preferably is selected from the group consisting of halo, hydrocarbyl, silyl, and N,N-dialkylamino-substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral L ligand group may be present.

R$^1$ each occurrence preferably is hydrogen or a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two R$^1$ groups may be joined together;

Z in all of the foregoing embodiments preferably is
—Y—Z'— wherein;
Y is —O—, —S—, —NR$^5$—, —PR$^5$—; —NR$^5_2$, or
—PR$^5_2$;
Z' is SiR$^6_2$, CR$^6_2$, SiR$^6_2$SiR$^6_2$, CR$^6_2$CR$^6_2$, CR$^6$=CR$^6$,
CR$^6_2$SiR$^6_2$, BR$^6$, BR$^6$L", or GeR$^6_2$;
R$^5$ each occurrence is independently hydrocarbyl,
trihydrocarbylsilyl, or trihydrocarbylsilylhydrocarbyl,
said R$^5$ having up to 20 atoms other than hydrogen, and
optionally two R$^5$ groups or R$^5$ together with Y form a
ring system;
R$^6$ each occurrence is independently hydrogen, or a
member selected from hydrocarbyl, hydrocarbyloxy,
silyl, halogenated alkyl, halogenated aryl, —NR$^5_2$, and
combinations thereof, said R$^6$ having up to 20 non-
hydrogen atoms, and optionally, two R$^6$ groups form a
ring system. Preferred R$^6$ groups include alkyl,
cycloalkyl, aryl, aralkyl, trihydrocarbylsilyl, or
trihydrocarbylsilylhydrocarbyl, and alkaryl groups of
up to 10 carbons.

Most preferably Z is —Si(CH$_3$)$_2$—N(C(CH$_3$)$_3$— or —Si
(p—C$_6$H$_4$CH$_3$)$_2$—N(C(CH$_3$)$_3$—;

Polycyclic, fused ring, heteroatom containing ligands for
use in the preparation of the present metal complexes
may be readily prepared from known compounds by
one skilled in the art, using published techniques or
techniques analogous to published techniques.

Illustrative metal complexes that may be employed in the
practice of the present invention include the following
compounds corresponding to formula IF:
(t-butylamido)dimethyl-[6,7]benzo-[4,5:2',3'](1-
methylisoindol)-(3H)-indene-2-yl)silanetitanium (II) 1,4-
diphenyl-1,3-butadiene,
(t-butylamido)dimethyl-[6,7]benzo-[4,5:2',3'](1-
methylisoindol)-(3H)-indene-2-yl)silanetitanium (II) 1,3-
pentadiene,
(t-butylamido)dimethyl-[6,7]benzo-[4,5:2',3'](1-
methylisoindol)-(3H)-indene-2-yl)silanetitanium (III)
2-(N,N-dimethylamino)benzyl,
(t-butylamido)dimethyl-[6,7]benzo-[4,5:2',3'](1-
methylisoindol)-(3H)-indene-2-yl)silanetitanium (IV)
dichloride,
(t-butylamido)dimethyl-[6,7]benzo-[4,5:2',3'](1-
methylisoindol)-(3H)-indene-2-yl)silanetitanium (IV)
dimethyl,
(t-butylamido)dimethyl-[6,7]benzo-[4,5:2',3'](1-
methylisoindol)-3H)-indene-2-yl)silanetitanium (IV)
dibenzyl,
(t-butylamido)dimethyl-[6,7]benzo-[4,5:2',3'](1-
methylisoindol)-(3H)-indene-2-yl)silanetitanium (IV) bis
(trimethylsilyl),
(cyclohexylamido)dimethyl-[6,7]benzo-[4,5:2',3'](1-
methylisoindol)-(3H)-indene-2-yl)silanetitanium (II) 1,4-
diphenyl-1,3-butadiene,
(cyclohexylamido)dimethyl-[6,7]benzo-[4,5:2',3'](1-
methylisoindol)-(3H)-indene-2-yl)silanetitanium (II) 1,3-
pentadiene,
(cyclohexylamido)dimethyl-[6,7]benzo-[4,5:2',3'](1-
methylisoindol)-(3H)-indene-2-yl)silanetitanium (III)
2-(N,N-dimethylamino)benzyl,
(cyclohexylamido)dimethyl-[6,7]benzo-[4,5:2',3'](1-
methylisoindol)-(3H)-indene-2-yl)silanetitanium (IV)
dichloride,
(cyclohexylamido)dimethyl-[6,7]benzo-[4,5:2',3'](1-
methylisoindol)-(3H)-indene-2-yl)silanetitanium (IV)
dimethyl,
(cyclohexylamido)dimethyl-[6,7]benzo-[4,5:2',3'](1-
methylisoindol)-(3H)-indene-2-yl)silanetitanium (IV)
dibenzyl,
(cyclohexylamido)dimethyl-[6,7]benzo-[4,5:2',3'](1-
methylisoindol)-(3H)-indene-2-yl)silanetitanium (IV) bis
(trimethylsilyl),
(t-butylamido)di(p-methylphenyl)-[6,7]benzo-[4,5:2',3'](1-
methylisoindol)-(3H)-indene-2-yl)silanetitanium (II) 1,4-
phenyl-1,3-butadiene,
(t-butylamido)di(p-methylphenyl)-[6,7]benzo-[4,5:2',3'](1-
methylisoindol)-(3H)-indene-2-yl)silanetitanium (II) 1,3-
pentadiene,
(t-butylamido)di(p-methylphenyl)-[6,7]benzo-[4,5:2',3'](1-
methylisoindol)-(3H)-indene-2-yl)silanetitanium (III)
2-(N,N-dimethylamino)benzyl,
(t-butylamido)di(p-methylphenyl)-[6,7]benzo-[4,5:2',3'](1-
methylisoindol)-(3H)-indene-2-yl)silanetitanium (IV)
dichloride,
(t-butylamido)di(p-methylphenyl)-[6,7]benzo-[4,5:2',3'](1-
methylisoindol)-(3H)-indene-2-yl)silanetitanium (IV)
dimethyl,
(t-butylamido)di(p-methylphenyl)-[6,7]benzo-[4,5:2',3'](1-
methylisoindol)-(3H)-indene-2-yl)silanetitanium (IV)
dibenzyl,
(t-butylamido)di(p-methylphenyl)-[6,7]benzo-[4,5:2',3'](1-
methylisoindol)-(3H)-indene-2-yl)silanetitanium (IV) bis
(trimethylsilyl),
(cyclohexylamido)di(p-methylphenyl)-[6,7]benzo-[4,5:2',
3'](1-methylisoindol)-(3H)-indene-2-yl)silanetitanium
(II) 1,4-diphenyl-1,3-butadiene,
(cyclohexylamido)di(p-methylphenyl)-[6,7]benzo-[4,5:2',
3'](1-methylisoindol)-(3H)-indene-2-yl)silanetitanium
(II) 1,3-pentadiene,
(cyclohexylamido)di(p-methylphenyl)-[6,7]benzo-[4,5:2',
3'](1-methylisoindol)-(3H)-indene-2-yl)silanetitanium
(III) 2-(N,N-dimethylamino)benzyl,
(cyclohexylamido)di(p-methylphenyl)-[6,7]benzo-[4,5:2',
3'](1-methylisoindol)-(3H)-indene-2-yl)silanetitanium
(IV) dichloride,
(cyclohexylamido)di(p-methylphenyl)-[6,7]benzo-[4,5:2',
3'](1-methylisoindol)-(3H)-indene-2-yl)silanetitanium
(IV) dimethyl,
(cyclohexylamido)di(p-methylphenyl)-[6,7]benzo-[4,5:2',
3'](1-methylisoindol)-(3H)-indene-2-yl)silanetitanium
(IV) dibenzyl, and
(cyclohexylamido)di(p-methylphenyl)-[6,7]benzo-[4,5:2',
3'](1-methylisoindol)-(3H)-indene-2-yl)silanetitanium
(IV) bis(trimethylsilyl).

The complexes can be prepared by combining a Group 4 metal tetrahalide or tetraamide salt with the corresponding polycyclic ring system ligand dianion in an inert diluent. Optionally a reducing agent can be employed to produce the lower oxidation state complexes, and standard ligand exchange procedures can by used to produce different ligand substituents. Processes that are suitably adapted for use herein are well known to synthetic organometallic chemists. The syntheses are preferably conducted in a suitable non-interfering solvent at a temperature from −100 to 300° C., preferably from −78 to 100° C., most preferably from 0 to 50° C. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof, aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

Polycyclic, fused ring, heteroatom containing compounds suitable as starting reagents for the present metal complexes may be synthesized using standard organic synthetic procedures. For example, nitrogen containing compounds can be prepared from hydrazine and polycyclic ketones in a process analogous to those disclosed in *J. Heterocyclic Chem.*, 25, 671 (1988) for preparing alkylbenzocarbazoles from tetralone and hydrazine.

The complexes are rendered catalytically active by combination with an activating cocatalyst (B). Suitable activating cocatalysts for use herein include polymeric or oligomeric alumoxanes, especially methylalumoxane (MAO), triisobutyl aluminum modified methylalumoxane (MMAO), or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; and combinations of the foregoing activating cocatalysts. The foregoing activating cocatalysts have been previously taught with respect to different metal complexes in the following references: U.S. Pat. No. 5,153,157, U.S. Pat. No. 5,064,802, U.S. Pat. No. 5,321,106, U.S. Pat. No. 5,350,723, and U.S. Pat. No. 5,721,185.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoropheny-borane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

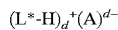

wherein:

L* is a neutral Lewis base;

(L*-H)⁺ is a conjugate Bronsted acid of L*;

$A^{d-}$ is a noncoordinating, compatible anion having a charge of d−; and d is an integer from 1 to 3.

More preferably $A^{d-}$ corresponds to the formula: $[M'Q_4]^-$; wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is A⁻. Activating cocatalysts comprising boron which are particularly useful in the preparation of catalysts of this invention may be represented by the following general formula:

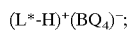

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups. Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:
trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-diethylanilinium pentafluorophenoxytris(pentafluorophenyl) borate,
N,N-diethylanilinium tetrakis(pentafluorophenyl) borate,
N,N-dimethyl-2,4,6-trimethylanilinium tetrakis(pentafluorophenyl) borate,
dimethyloctadecylammonium tetrakis(pentafluorophenyl) borate,
methyldioctadecylammonium tetrakis(pentafluorophenyl) borate,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate,
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis(pentafluorophenyl) borate,
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate,
di-substituted sulfonium salts such as:
di(o-tolyl)sulfonium tetrakis(pentafluorophenyl) borate, and
methylcotadecylsulfonium tetrakis(pentafluorophenyl) borate.

Preferred (L*-H)$^+$ cations are methyldioctadecylammonium cations, dimethyloctadecylammonium cations, and ammonium cations derived from mixtures of trialkyl amines containing one or 2 $C_{14-18}$ alkyl groups.

Another suitable ion forming, activating cocatalyst comprises a salt of a cationic oxidizing agent and a noncoordinating, compatible anion represented by the formula:

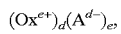

$$(Ox^{e+})_d(A^{d-})_e,$$

wherein:
Ox$^{e+}$ is a cationic oxidizing agent having a charge of e+;
e is an integer from 1 to 3; and
A$^{d-}$ and d are as previously defined.

Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$[C]^+A^-$$

wherein:
[C]$^+$ is a $C_{1-20}$ carbenium ion; and
A$^-$ is as previously defined. A preferred carbenium ion is the trityl cation, that is triphenylmethylium.

A further suitable ion forming, activating cocatalyst comprises a compound which is a salt of a silylium ion and a noncoordinating, compatible anion represented by the formula:

$$(R^6{}_3Si)^+A^-$$

wherein:
R$^6$ is $C_{1-10}$ hydrocarbyl, and A$^-$ is as previously defined.

Preferred silylium salt activating cocatalysts are trimethylsilylium tetrakispentafluorophenylborate, triethylsilylium tetrakispentafluorophenylborate and ether substituted adducts thereof. Silylium salts have been previously generically disclosed in *J. Chem Soc. Chem, Comm.*, 1993, 383–384, as well as Lambert, J. B., et al., *Organometallics*, 1994, 13, 2430–2443. The use of the above silylium salts as activating cocatalysts for addition polymerization catalysts is disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)-borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The resulting catalysts may be used to polymerize ethylenically and/or acetylenically unsaturated monomers having from 2 to 100,000 carbon atoms either alone or in combination. The monomers for use herein include aliphatic and aromatic compounds containing vinylic unsaturation, as well as cyclic unsaturated compounds such as cyclobutene, cyclopentene, and norbornene, including norbornene substituted in the 5 and 6 position with $C_{1-20}$ hydrocarbyl groups, and $C_{6-40}$ diolefins. Also included are mixtures of such monomers, especially mixtures of $C_{2-8}$ olefins with $C_{6-40}$ diolefin compounds. Examples of suitable $C_{6-40}$ diolefin compounds include ethylidenenorbornene, 1,4-hexadiene, and norbornadiene. Long chain vinyl terminated monomers may be formed during the polymerization process, for example by the phenomenon of δ-hydride elimination of a proton from a growing polymer chain. This process results in incorporation of such extremely long chains of preformed polymer into the resulting polymer, that is long chain branching.

Vinylaromatic monomers for use herein include $C_{8-20}$ aryl substituted ethylene compounds having the formula:

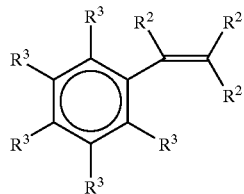

wherein:
$R^2$ independently each occurrence is hydrogen or $C_{1-4}$ alkyl, and
$R^3$ independently each occurrence is $R^2$ or halo.

Preferred monomers include the $C_{2-20}$ olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, norbornene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene.

More preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{6-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a $C_{6-40}$ nonconjugated diene, especially ethylidenenorbornene or 1,4-hexadiene.

In one preferred embodiment of the invention a conjugated diene having 4 or 5 carbons, especially 1,3-butadiene, 1,3-pentadiene, or 3-methyl-1,3-butadiene, is added to the polymerization mixture in a molar ratio compared to addition polymerizable olefin compound of from 1:100,000 to 1:4.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed to support the metal complex, cocatalyst, the reaction product of the catalyst and cocatalyst, or all of the foregoing, when the catalysts are used in a gas phase polymerization process. The support is preferably employed in an amount to provide a weight ratio of catalyst (based on metal): support from 1:100,000 to 1:10, more preferably from 1:50,000 to 1:20, and most preferably from 1:10,000 to 1:30.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500, equivalent to U.S. Ser. No. 07/904,770, as well as U.S. Ser. No. 08/10958, filed Jan. 29, 1993.

Utilizing the present catalyst compositions, interpolymers of ethylene, one or more vinylaromatic monomers and optionally an α-olefin or a diolefin having densities from 0.85 g/cm³ to 1.1 g/cm³, melt flow rates from 0.01 to 20.0 dg/min, and incorporating large amounts of vinylaromatic monomer in a pseudo-random manner are readily attained in a highly efficient process. Pseudo-random incorporation of vinylaromatic monomers is a well known phenomena in which the monomer is essentially randomly incorporated into the polymer, excepting that two such vinylaromatic monomers having the same orientation may not succeed one another in the polymer chain. The procedure has been previously disclosed in U.S. Pat. No. 5,703,187.

The catalyst compositions of the present invention are also particularly advantageous for the production of ethylene homopolymers, ethylene/α-olefin copolymers, and interpolymers of ethylene, a diene, and optionally a $C_{3-20}$ α-olefin having high levels of long chain branching and comonomer incorporation. The use of the catalysts of the present invention in continuous polymerization processes, especially continuous, solution polymerization processes, allows for elevated reactor temperatures which favor the formation of vinyl terminated polymer chains that may be incorporated into a growing polymer, thereby giving a long chain branch. The use of the present catalyst compositions advantageously allows for the economical production of ethylene/α-olefin copolymers having processability similar to high pressure, free radical produced low density polyethylene.

The catalyst composition may be prepared as a homogeneous catalyst by addition of the requisite components to a solvent in which polymerization will be carried out by solution polymerization procedures. The catalyst composition may also be prepared and employed as a heterogeneous catalyst by adsorbing the requisite components on an inert inorganic or organic particulated solid, as previously disclosed. In an preferred embodiment, a heterogeneous catalyst is prepared by co-precipitating the metal complex and the reaction product of an inert inorganic compound and an active hydrogen containing activator, especially the reaction product of a tri ($C_{1-4}$ alkyl) aluminum compound and an ammonium salt of a hydroxyaryltris(pentafluorophenyl)

borate, such as an ammonium salt of (4-hydroxy-3,5-ditertiarybutylphenyl)tris(pentafluorophenyl)borate.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably at least a major part of the diluent comprises the α-olefin monomer or monomers to be polymerized.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas such as, for example, nitrogen.

The polymerization may be carried out as a batchwise or a continuous polymerization process. A continuous process is preferred, in which event catalyst, ethylene, comonomer, and optionally solvent are continuously supplied to the reaction zone and polymer product continuously removed therefrom.

Without limiting in any way the scope of the invention, one means for carrying out such a polymerization process is as follows. In a stirred-tank reactor, the monomers to be polymerized are introduced continuously together with solvent and an optional chain transfer agent. The reactor contains a liquid phase composed substantially of monomers together with any solvent or additional diluent and dissolved polymer.

Catalyst (A) and cocatalyst (B) are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mentioned chain transfer agent, such as a stream of hydrogen introduced to the reactor, as is well known in the art. The reactor effluent is contacted with a catalyst kill agent such as water, steam or an alcohol. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours. By using a catalyst that incorporates large amounts of hindered monovinyl monomer, such as a vinylaromatic monomer, hindered monovinyl homopolymer formed from residual quantities of the monomer are substantially reduced.

The catalyst compositions of the invention are capable of producing ES interpolymers having highly uniform vinylaromatic monomer incorporation. Such uniform ES interpolymers are characterized by a unique $^{13}C$ NMR signature. In particular, such polymers are characterized by a cluster index, $CI_{ES}$, which relates a ratio of two peaks in the $^{13}C$ NMR spectrum, $NMR_F/NMR_E$, wherein $NMR_F$ is the integrated area of the peak associated only with vinylaromatic monomer/ethylene/vinylaromatic monomer (SES) triads (commonly appearing at approximately 25 to 26.9 ppm) and $NMR_E$ is the integrated area of the peak associated only with triads containing a single incorporated vinylaromatic monomer (commonly appearing at approximately 27 to 29 ppm). It should be emphasized that in both types of polymers the vinylaromatic monomer is incorporated in a pseudo random manner, that is, successive or adjacent head to tail insertion of a vinyl aromatic monomer in the polymer chain is still prohibited. Such pseudo random nature characteristically produces a $^1H$ NMR spectrum of the polymer which lacks any appreciable peaks between the two peaks located at approximately 37 and 46 ppm respectively. However, in uniform ES polymers, lack of clustering of the incorporated vinylaromatic monomer into alternating monomer sequences can be identified by comparing the area of the $NMR_E$ peaks relative to $NMR_F$ peaks as a function of monomer composition in the polymer.

This cluster index, $CI_{ES}$, can be expressed mathematically through use of the following formula:

$$CI_{ES} = \left[\frac{NMR_F}{NMR_E}\right]\left[\frac{(4F_1 - 2)}{(1 - F_1)}\right]$$

where $F_1$ is the mole fraction of ethylene in the polymer. The uniform pseudo-random ES polymers of the invention are characterized by $CI_{ES}$ values less than 1.0 at polymer compositions of less than 50 mole percent polymerized vinylaromatic monomer, preferably $CI_{ES}$ values less than 0.95 at compositions of less than 47 mole percent polymerized vinylaromatic monomer.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. All syntheses were performed under dry nitrogen atmosphere using a combination of glove box and high vacuum techniques. The term "overnight" refers to a period of time from 14 to 20 hours. The term "room ternperature" refers to a temperature from 20 to 25° C. In the event any compound depicted by a structural formula is incorrectly named, the formula shall be controlling.

Example 1

Synthesis of (t-butylamido)dimethyl(1H)-[4,5]benzo-[6,7,2',3'](1-methylisoindol)-indene-2-yl)silanetitanium (IV) dichloride also referred to as (1, 2, 3, 3a, 12c-η)-(1H)-[4,5]benzo-[6,7:2',3'](1-methylisoindol)indene-2-yl)-N-(1,1-dimethylethyl)-1,1-dimethylsilanamato (2-)-κN]dichloro titanium

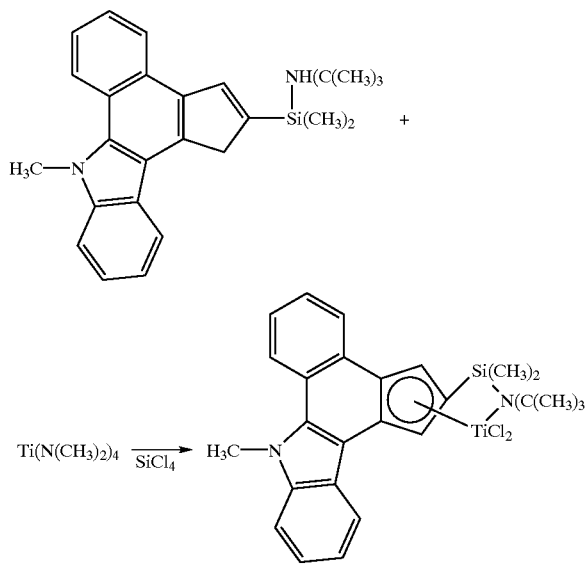

3H-Benz[e]indene-5-(4H)-one and N-methylaniline are reacted substantially according to the technique of *J. Heterocyclic Chem.* 25, 671 (1988) to prepare [6,7]benzo-[4,5:2',3'](1-methylisoindol)-(3H)-indene, which is subsequently converted to (t-butylamino)dimethyl-[6,7]benzo-[4,5:2',3'](1-methylisoindol)-(3H)-indene-2-yl)silane by reaction of the lithium salt with dimethyl(t-butylamino)chlorosilane. The resulting fused ring compound (0.700 g, 1.756 mmol) and titanium tetrakis(dimethylamide) (0.393 g, 1.756 mmol) are dissolved in 70 mL of n-octane and the solution heated to reflux for 24 hours. The solution is then cooled and 0.5 mL of silicon tetrachloride (4 mmol) added. After one hour the solid which forms is collected by vacuum filtration. This residue is slurried in mixed hexanes and toluene is added until most of the solid dissolves. The mixture is filtered and volatile materials are removed under reduced pressure. The solid residue is slurried again in mixed hexanes and the solid collected by filtration and dried under reduced pressure to give 0.416 g of a bright orange solid. The resulting $^1$H NMR and $^{13}$C NMR spectra are consistent with those expected of the desired compound.

Example 2

Synthesis of (t-butylamido)dimethyl(1H-[4,5]benzo-[6,7,2',3'](1-methylisoindol)-indene-2-yl)silanetitanium (IV) dimethyl.

To 0.400 g, 0.776 mmol, of (t-butylamido)dimethyl(1H-[4,5]benzo-[6,7,2',3'](1-methylisoindol)-indene-2-yl)silanetitanium (IV) dichloride dissolved in 40 mL of diethylether is added 0.55 mL of methylmagnesium bromide solution in diethylether (3.0 M). The solution darkens and a precipitate forms. After 2 hours the volatile materials are removed under reduced pressure. The residue is extracted twice with a total of 60 mL of hexanes. The hexanes extracts are filtered and volatile materials removed from the combined extracts under reduced pressure to give 0.165 g of a bright yellow microcrystalline solid. The resulting $^1$H NMR and $^{13}$C NMR spectra are consistent with those expected of the desired compound.

Polymerization

Ethylene and styrene are copolymerized in the following manner. A two-liter Parr reactor equipped with a mechanical stirrer is charged with appropriate amounts of toluene solvent and styrene comonomer. Hydrogen is added (Δ10 psi, Δ70 kPa) as a molecular weight control agent by differential pressure expansion from a 75 mL addition tank at 275 psig (1.9 MPa). The reactor is heated to 130° C. and saturated with ethylene at 4.5 MPa pressure. The appropriate amount of catalyst and trispentafluorophenylborane cocatalyst as 0.005 M toluene solutions are premixed in a glovebox to give a 1:3 molar ratio of catalyst and cocatalyst based on boron and transferred to a catalyst addition tank and injected into the reactor. The polymerization conditions are maintained for ten minutes while controlling the reactor temperature at the desired level and supplying ethylene on demand.

After polymerization for the indicated time period, the resulting solution is removed from the reactor into a nitrogen purged collection vessel containing 20 ml of a 10 weight percent toluene solution of hindered phenol antioxidant (Irganox™ 1010 from Ciba Geigy Corporation) and phosphorus stabilizer (Irgafos™ 168, also from Ciba-Geigy Corporation). Polymers formed are dried in a programmed vacuum oven with a maximum temperature of 145° C. and an overnight heating cycle. Results are shown in Table 1.

TABLE 1

| Run | Catalyst | Efficiency (g polymer/g Ti) | Mole Percent Styrene Incorporation |
|---|---|---|---|
| A* | Comp.[1] | 410,000 | 12 |
| B | Ex. 2 | 530,000 | 10 |
| C* | Comp.[1] | 480,000 | 12 |

*Comparative, not an example of the invention
[1](1H-cyclopenta[l]phenanthrene-2-yl)dimethyl(t-butylamido)silanetitanium dimethyl, prepared according to the teachings of U.S. Pat. No. 6,150,297.

What is claimed is:

1. A metal complex corresponding to the formula:

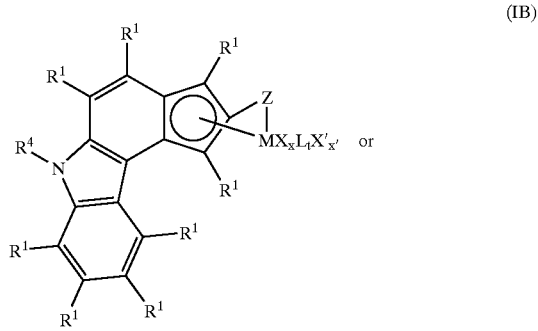

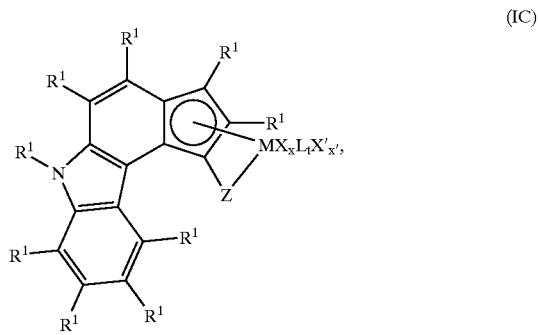

where M is titanium, zirconium or hafnium in the +2, +3 or +4 formal oxidation state;

$R^1$ independently each occurrence is hydrogen, hydrocarbyl, trihydrocarbylsilyl, trihydrocarbylsilylhydrocarbyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring;

$R^4$ is hydrocarbyl, silyl, germyl, or halohydrocarbyl or up to 10 atoms other than hydrogen;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

t is a number from 0 to 2, and x' is 0 or 1.

2. A metal complex corresponding to the formula:

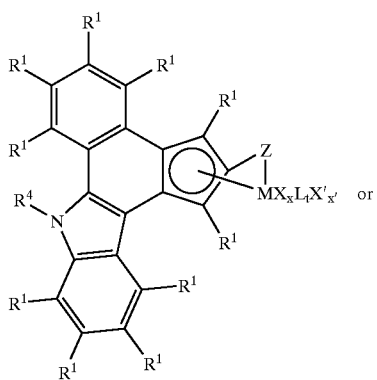

(ID)

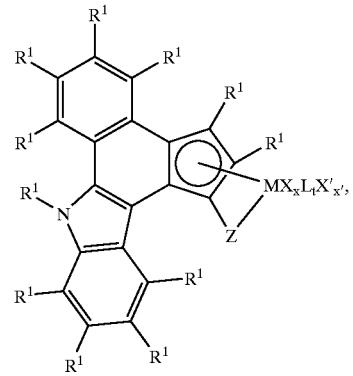

(IE)

wherein,

M is titanium in the +2, +3 or +4 formal oxidation state;

$R^1$ independently each occurrence is hydrogen or $C_{1-10}$ hydrocarbyl, and optionally two or more of the foregoing adjacent $R^1$ groups may together form a divalent derivative thereby forming a saturated or unsaturated fused ring;

$R^4$ is $C_{1-4}$ alkyl;

Z is a divalent moiety lacking in delocalized electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

t is a number from 0 to 2, and x' is 0 or 1.

3. The metal complex according to claim 2, corresponding to the formula:

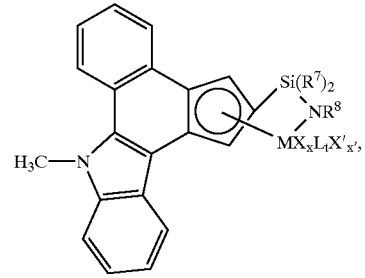

(IF)

wherein,

M is titanium in the +2 or +4 formal oxidation state;

$R^7$ independently each occurrence is $C_{1-10}$ hydrocarbyl;

$R^8$ is $C_{1-10}$ alkyl or cycloalkyl;

X is a chloride, $C_{1-4}$ alkyl or benzyl;

L independently each occurrence is a neutral ligating compound having up to 20 atoms;

X' is 1,4-butanediyl or (2,3-dimethyl-1,4-butanediyl);

x is 0 or 2;

t is a number from 0 to 2, and x' is 0 or 1.

4. A metal complex according to claim 3 selected from the group consisting of:

(t-butylamido)dimethyl-[6,7]benzo-[4,5:2',3'](1-methylisoindol)-(3H)-indene-2-yl)silanetitanium (II) 1,4-diphenyl-1,3-butadiene, (t-butylamido)dimethyl-[6,7]benzo-[4,5:2',3'](1-methylisoindol)-(3H)-indene-2-yl)silanetitanium (II) 1,3-pentadiene, (t-butylamido)dimethyl-[6,7]benzo-[4,5:2',3'](1-methylisoindol)-(3H)-indene-2-yl)silanetitanium (II) 2-(N,N-dimethylamino)benzyl, (t-butylamido)dimethyl-[6,7]benzo-[4,5:2',3'](1-methylisoindol)-(3H)-indene-2-yl)silanetitanium (IV) dichloride, (t-butylamido)dimethyl-[6,7]benzo-[4,5:2',3'](1-methylisoindol)-(3H)-indene-2-yl)silanetitanium (IV) dimethyl, (t-butylamido)dimethyl-[6,7]benzo-[4,5:2',3'](1-methylisoindol)-(3H)-indene-2-yl)silanetitanium (IV) dibenzyl, (cyclohexylamido)dimethyl-[6,7]benzo-[4,5:2',3'](1-methylisoindol)-(3H)-indene-2-yl)silanetitanium (II) 1,4-diphenyl-1,3-butadiene, (cyclohexylamido)dimethyl-[6,7]benzo-[4,5:2',3'](1-methylisoindol)-(3H)-indene-2-yl)silanetitanium (II) 1,3-pentadiene, (cyclohexylamido)dimethyl-[6,7]benzo-[4,5:2',3'](1-methylisoindol)-(3H)-indene-2-yl)silanetitanium (III) 2-(N,N-dimethylamino)benzyl, (cyclohexylamido)dimethyl-[6,7]benzo-[4,5:2',3'](1-methylisoindol)-(3H)-indene-2-yl)silanetitanium (IV) dichloride, (cyclohexylamido)dimethyl-[6,7]benzo-[4,5:2',3'](1-methylisoindol)-(3H)-indene-2-yl)silanetitanium (IV) dimethyl, (cyclohexylamido)dimethyl-[6,7]benzo-[4,5:2',3'](1-methylisoindol)-3H)-indene-2-yl)silanetitanium (IV) dibenzyl, (t-butylamido)di(p-methylphenyl)-[6,7]benzo-[4,5:2',3'](1-methylisoindol)-(3H)-indene-2-yl)silanetitanium (II) 1,4-diphenyl-1,3-butadiene, (t-butylamido)di(p-methylphenyl)-[6,7]benzo-[4,5:2',3'](1-methylisoindol)-(3H)-indene-2-yl)silanetitanium (II) 1,3-pentadiene, (t-butylamido)di(p-methylphenyl)-[6,7]benzo-[4,5:2',3'](1-methylisoindol)-(3H)-indene-2-yl)silanetitanium (III) 2-(N,N-dimethylamino)benzyl, (t-butylamido)di(p-methylphenyl)-[6,7]benzo-[4,5:2',3'](1-methylisoindol)-(3H)-indene-2-yl)silanetitanium (IV) dichloride, (t-butylamido)di(p-methylphenyl)[6,7]benzo-[4,5:2',3'](1-methylisoindol)-(3H)-indene-2-yl)silanetitanium (IV) dimethyl, (t-butylamido)di(p-methylphenyl)-[6,7]benzo-[4,5:2',3'](1-methylisoindol)-(3H)-indene-2-yl)silanetitanium (IV) dibenzyl, (cyclohexylamido)di(p-methylphenyl)-[6,7]benzo-[4,5:2',3'](1-methylisoindol)-(3H)-indene-2-yl)silanetitanium (II) 1,4-diphenyl-1,3-butadiene, (cyclohexylamido)di(p-methylphenyl)-[6,7]benzo-[4,5:2',3'](1-methyl isoindol)-(3H)-indene-2-yl)silanetitanium (II) 1,3-pentadiene, (cyclohexylamido)di(p-methylphenyl)-[6,7]benzo-[4,5:2',3'](1-methylisoindol)-(3H)-indene-2-yl)silanetitanium (III) 2-(N,N-dimethylamino)benzyl, (cyclohexylamido)di(p-methylphenyl)[6,7]benzo-[4,5:2',3'](1-methylisoindol)-(3H)-indene-2-yl)silanetitanium (IV) dichloride, (cyclohexylamido)di(p-methylphenyl)-[6,7]benzo-[4,5:2',3'](1-methylisoindol)-(3H)-indene-2-yl)silanetitanium (IV) dimethyl, and (cyclohexylamido)di(p-methylphenyl)-[6,7]benzo-[4,5:2',3'](1-methylisoindol)-(3H)-indene-2-yl)silanetitanium (IV) dibenzyl.

5. A process for the polymerization of an addition polymerizable monomer or monomer mixture comprising contacting said monomer or mixture of monomers under addition polymerization conditions with a catalyst composition comprising the reaction product or admixture of:

(A) a metal complex according to any one of claims 1–4; and (B) a cocatalyst that forms an active polymerization catalyst species in combination with (A).

6. The process of claim 5 wherein an olefin monomer or a mixture of olefin monomers is polymerized.

7. The process of claim 6 wherein ethylene and a vinylaromatic monomer are copolymerized.

8. The process of claim 7 wherein ethylene and styrene are copolymerized.

\* \* \* \* \*